United States Patent [19]
Miller, Jr.

[11] 3,939,714
[45] Feb. 24, 1976

[54] VARIABLE PERCENTAGE SAMPLER
[75] Inventor: William H. Miller, Jr., Knoxville, Tenn.
[73] Assignee: The United States of America as represented by the United States Energy Research and Development Administration, Washington, D.C.
[22] Filed: June 10, 1975
[21] Appl. No.: 585,626

[52] U.S. Cl. ................................................. 73/424
[51] Int. Cl.² ........................................... G01N 1/20
[58] Field of Search ...................................... 73/424

[56] References Cited
UNITED STATES PATENTS
1,646,032  10/1927  Mason ................................. 73/424
2,076,188  4/1939  Thorsten .............................. 73/424

Primary Examiner—S. Clement Swisher
Attorney, Agent, or Firm—Dean E. Carlson; David S. Zachry; Louis M. Deckelmann

[57] ABSTRACT

A remotely operable sampler is provided for obtaining variable percentage samples of nuclear fuel particles and the like for analyses. The sampler has a rotating cup for a sample collection chamber designed so that the effective size of the sample inlet opening to the cup varies with rotational speed. Samples of a desired size are withdrawn from a flowing stream of particles without a deterrent to the flow of remaining particles.

4 Claims, 2 Drawing Figures

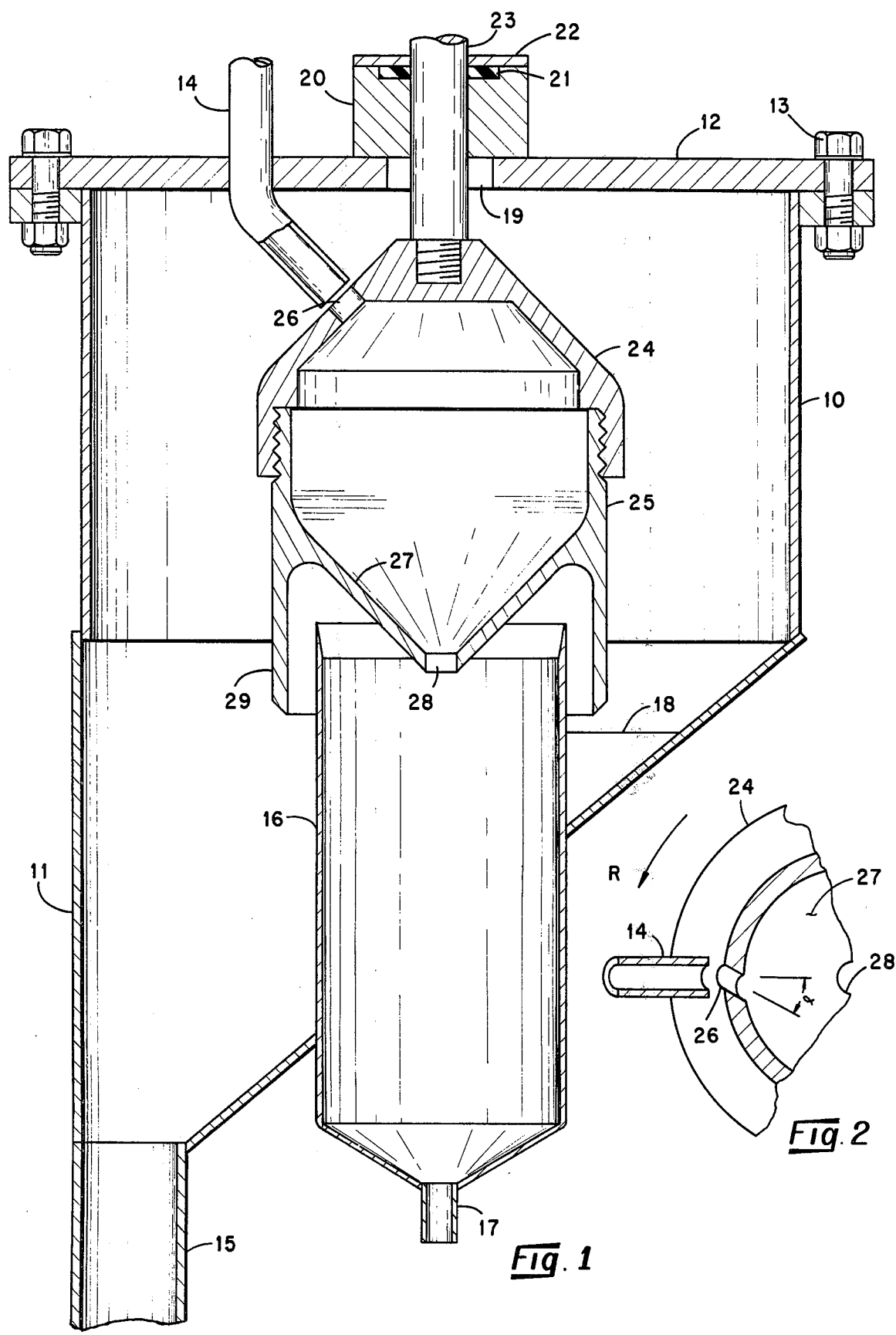

VARIABLE PERCENTAGE SAMPLER

BACKGROUND OF THE INVENTION

This invention was made in the course of, or under, a contract with the Energy Research and Development Administration.

In the fabrication of nuclear fuel microspheres it is necessary to perform certain analyses on random samples withdrawn from a bulk supply. One such analysis or test is the measurement of individual particle diameter to ascertain size distribution. Preferably these tests are performed beginning with the bare fuel kernel and then after the deposition of any coatings such as the pyrolytic carbon coating applied to most particles. The initial kernel may be, for example, about 380 $\mu$m in diameter where the fully-coated particle may be about 800 $\mu$m. Other analyses, such as density, uniformity of size, etc., are typically performed at various stages of fabrication.

One problem that exists in connection with any of these analyses relates to the sampling technique whereby a representative sample of proper size is obtained. Furthermore, the desired size of the sample may vary for different analyses, or because of a different type particle. In addition, all sampling must be conducted remotely particularly when recycle material is being utilized due to higher radiation levels. Thus there exists a need for a remotely-operated variable-percentage sampler wherein the sampler will provide the desired size sample of particles for subsequent analyses. This need has been met in the present invention in a manner to be described hereinbelow.

SUMMARY OF THE INVENTION

It is the object of the present invention to provide a remotely-operated variable-percentage sampler wherein the desired size sample of particles may be collected for subsequent analysis.

The above object has been accomplished in the present invention by providing a rotating sample cup having a side hole therethrough. A particle feed tube is generally aligned with the cup side hole and a stream of particles is directed through the feed tube against the exterior of the rotating sample cup such that, during time intervals when the hole is aligned with the particle stream, particles pass through the hole into the cup interior. Thus, depending upon the shape, orientation of the hole, thickness of the sample cup wall, and the speed of cup rotation, the sample size is varied. Particles not entering the cup are collected to be carried to additional processing stages or storage.

BRIEF DESCRIPTION OF THE DRAWINGS

FIG. 1 is a vertical cross sectional view of the sampler.

FIG. 2 is an enlarged partial cross section view of the collection cup and particle feed tube of FIG. 1.

DESCRIPTION OF THE PREFERRED EMBODIMENT

Referring now to FIG. 1, a hopper is formed by a cylindrical upper shell 10 and a lower asymmetrical inverted conical shell 11. This hopper has a removable cover flange 12 attached thereto with bolts 13 or the like. Passing through flange 12 is at least one particle feed tube 14. A discharge conduit 15 is attached to the bottom of conical shell 11. An upright open-top sample receiving column 16 passes through and is sealed to conical shell 11 and is attached to a sample outlet conduit 17. A strengthening brace 18 is attached between column 16 and shell 11.

Mounted centrally over an opening 19 in the flange 12 is a bushing member 20 which is provided with a dust seal 21 under a cover 22. A shaft 23, attached to a drive means, not shown, passes through the cover 22, dust seal 21, and the bushing member 20 into the interior of the upper shell 10. Attached to this shaft 23 within shell 10 is a sample catcher which, in this embodiment, is formed by a conical cap 24 and a base 25 affixed thereto. The cap 24 is provided with an aperture 26 which is oriented perpendicularly to the shape of the outer surface of the cap 24, but slanted, inwardly, from a true radial orientation in a direction generally away from the direction of rotation as shown in FIG. 2 of the drawing. The tip of the particle feed tube 14 is oriented perpendicularly to the surface of cap 24 and terminates a short distance therfrom.

The base 25 of the sample catcher is provided with an interior inverted conical surface 27 to direct sample particles collected in the catcher through an opening 28 into the column 16. Depending upon the rotational speed of the catcher and the angle of surface 27, collected particles may be held in the catcher or discharged through the opening 28 during rotation of the catcher; higher speeds and larger included angles of the surface 27 tend to hold the collected particles, while lower speeds and a smaller included angle tend to continuously discharge particles. The base 25 is provided with a skirt 29 which overlaps the top of column 16 to minimize introduction of particles into column 16 which have not passed through the catcher.

Referring now to FIG. 2, the angular orientation of aperture 26 may be seen. As stated above, the aperture 26 is perpendicular to the slope of cap 24 but is oriented at an angle, $\alpha$, with respect to a true radial direction. The direction of angle $\alpha$, with respect to the radial direction, depends upon the direction of rotation, R, of the catcher. It may be seen that the aperture 26 is oriented in a reverse direction with regard to incoming particles and thus is not a scoop. Furthermore, the size of the angle $\alpha$, the shape of the aperture 26, and the thickness through cap 24 affect the sample size for a given rotational speed; larger angles and greater thickness reduce the size of the sample. Another method of increasing the sample size is to use additional feed tubes 14. Thus, for a given construction, sample size is only effected by rotational speed.

In a normal operation of the above described sampler, particles are fed continuously through the tube 14 from a particle supply, not shown, with the catcher being rotated typically at 100-250 RPM. The bulk of the particles strike the outer surface of cap 24 and fall down through shell 11 and out through conduit 15. Each time the aperture 26 passes the exit from the tube 14, a small portion of particles pass through the aperture into the body of the sample catcher and are removed through the opening 28, column 16, and conduit 17. As stipulated above, the size of the sample in proportion to the feed stream is determined by dimensions and orientation of aperture 26 as well as by the rotational speed of the catcher. For any given sampler, the sample size range is varied by varying the rotational speed. If any particles remain within the catcher, due to centrifugal forces, the catcher may be stopped or slowed whereupon the particles will drop out through opening 28 into column 16 and through conduit 17 to a collector, not shown. The samples so collected may be directed to appropriate analytical equipment, such as a particle size measuring apparatus.

A sampler of the above design was constructed having an aperture 26 in the catcher of ¼ inch diameter set at an angle $\alpha = 30°$. The thickness of the cap 24 was ⅛ inch, and its diameter was 3 inches. Particles in a size range of 417 to 500 μm were fed through a ¼ inch feed tube. When the catcher was rotated at 100 RPM, the sample size was 5.6% of the total microsphere batch fed into the sampler; with a speed of 250 RPM, the sample was 0.048% of the (2 kg) total batch. The size of the sample generally varied linearly between these values as a function of speed. Thus, it may be seen that a simple adjustment of speed provides samples of a variable percentage of the total available quantity of feed particles as a function of such speed.

It should be evident that the sampler described above is adapted to be remotely operated, thus minimizing any possible radiation exposure to operating personnel when the sampler is utilized for collection of radioactive particles.

This invention has been described by way of illustration rather than by limitation and it should be apparent that it is equally applicable in fields other than those described.

What is claimed is:

1. A sampler for obtaining variable percentage samples of particles for subsequent analyses comprising a hopper provided with a top closure member and a particle discharge conduit mounted at the lower end of an inverted conical lower shell portion of said hopper, a drive shaft extending through said top closure member into the upper portion of said hopper and being bearingly supported by said member, a conical cap affixed to the lower end of said drive shaft and provided with a side aperture, a base member affixed to said conical cap and provided with an inverted inner conical surface terminated by an exit hole at the bottom thereof, an open top sample receiving column extending through said conical shell portion of said hopper and affixed thereto with the top open end of said column encompassing the lower end of said base member for receiving particles exiting therefrom, said column being provided at its lower end with a sample outlet conduit, and a particle feed tube extending through said top closure member with its exit end positioned closely adjacent to and aligned with said side aperture of said conical cap, said conical cap and its affixed base member functioning as a particle sample catcher, said conical cap and base member affixed thereto adapted to be rotated by said drive shaft at a selected desired speed, whereby during rotation of said sample catcher a portion of the particles exiting from said feed tube are caught by said sample catcher through said side aperture as a function of the speed of rotation of said sample catcher.

2. The sampler set forth in claim 1, wherein said base member affixed to said conical cap is provided with a skirt which overlaps the open top of said sample receiving column to minimize introduction of particles into said column that did not pass through said sample catcher.

3. The sampler set forth in claim 2, wherein said side aperture of said conical cap is oriented at a selected angle with respect to a true radial direction and also in a reverse direction with regard to the direction of rotation of said sample catcher and to incoming particles from said feed tube.

4. The sampler set forth in claim 3, wherein said selected angle is 30°.

* * * * *